United States Patent [19]

Kenna

[11] Patent Number: 4,666,450
[45] Date of Patent: May 19, 1987

[54] ACETABULAR CUP ASSEMBLY PROSTHESIS

[75] Inventor: Robert V. Kenna, Hackensack, N.J.

[73] Assignee: Pfizer Hospital Products Group, Inc., New York, N.Y.

[21] Appl. No.: 526,726

[22] Filed: Aug. 26, 1983

[51] Int. Cl.[4] ............................................. A61F 2/34
[52] U.S. Cl. .................................................... 623/22
[58] Field of Search ........................ 3/1.9, 1.81, 1.912, 3/1.913; 128/92 C, 92 CA

[56] References Cited

U.S. PATENT DOCUMENTS

| D. 230,429 | 2/1974 | Davidson | D83/1 E |
|---|---|---|---|
| 3,685,058 | 8/1972 | Tronzo | 3/1 |
| 3,818,512 | 6/1974 | Shersher | 3/1 |
| 3,874,003 | 4/1975 | Moser et al. | 3/1 |
| 3,875,593 | 4/1975 | Shersher | 3/1 |
| 4,164,794 | 8/1979 | Spector et al. | 128/92 C |
| 4,262,369 | 4/1981 | Roux | 3/1.912 |

FOREIGN PATENT DOCUMENTS

| 2950536 | 7/1971 | Fed. Rep. of Germany | 3/1.913 |
|---|---|---|---|
| 2349357 | 4/1975 | Fed. Rep. of Germany | |
| 2845231 | 5/1979 | Fed. Rep. of Germany | 3/1.912 |
| 7202254 | 8/1973 | Netherlands | 3/1.912 |

Primary Examiner—Richard J. Apley
Assistant Examiner—David J. Isabella
Attorney, Agent, or Firm—Charles J. Knuth; Peter C. Richardson; Harold W. Ordway

[57] ABSTRACT

An acetabular cup assembly prosthesis comprises the combination of a support shell for introduction into an acetabulum and a socket insert in nesting engagement within the shell. The shell has a generally hemispherical outer surface and a downwardly extending concavity surrounded by a peripheral rim, At least one anchoring post secures the shell to the acetabulum, and a central opening in the bottom of the concavity serves as a connection location for the socket insert. The insert has a hemispherical concavity that articulates with the rounded head of a femoral prosthesis, while the outer surface of the insert nests within the concavity of the support shell. A central fastening tab extends from the insert into locking engagement with the opening in the support shell, and structure is provided to prevent relative rotation of the shell and insert.

13 Claims, 20 Drawing Figures

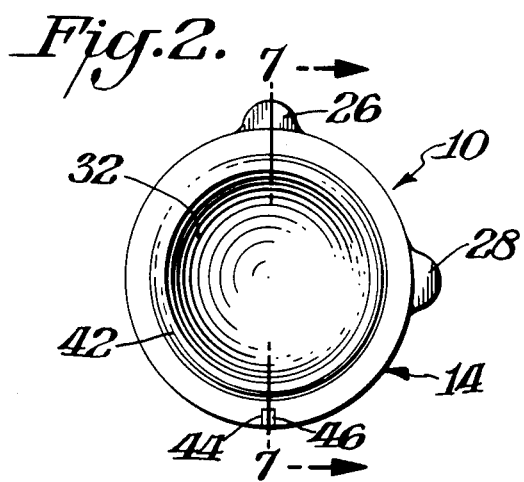
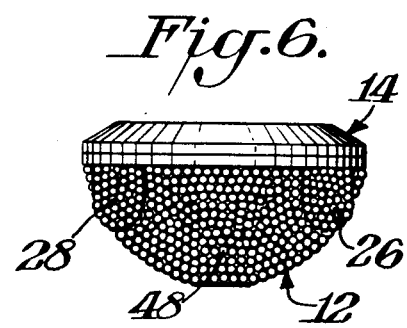
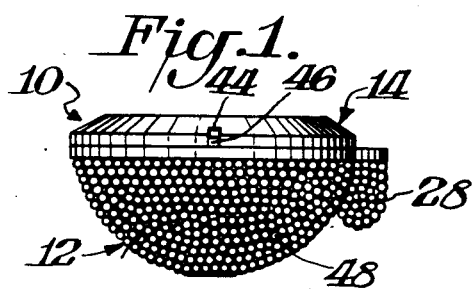
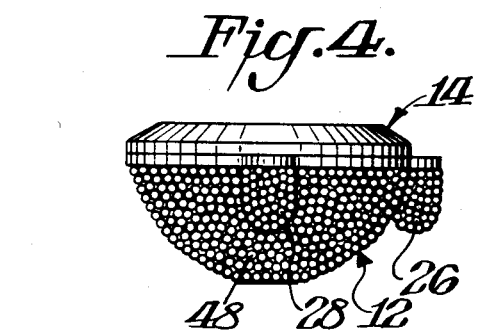
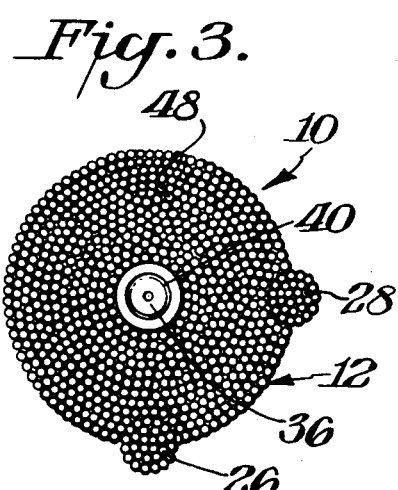
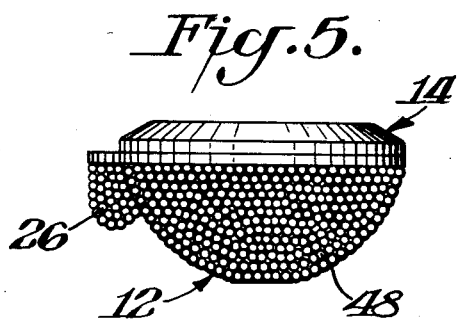
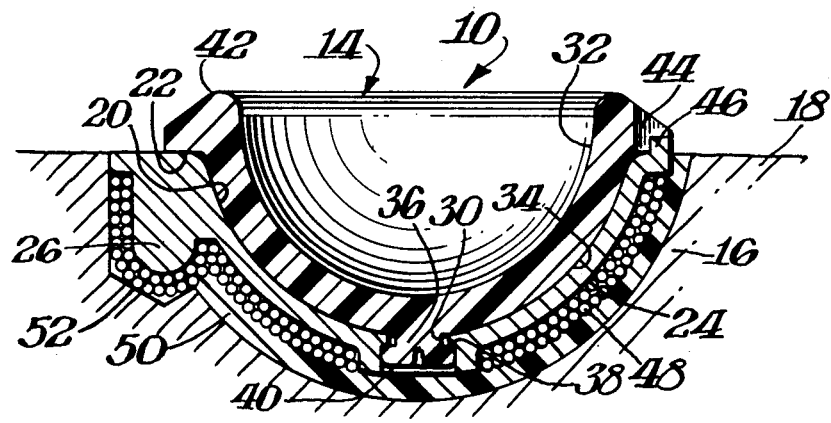

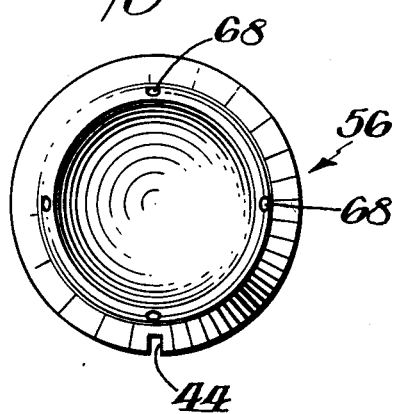
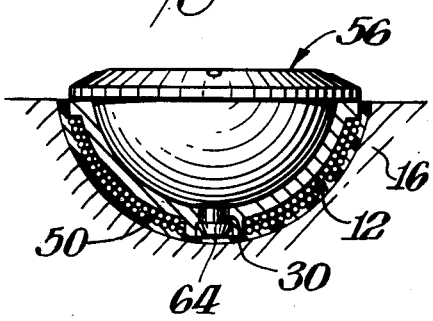
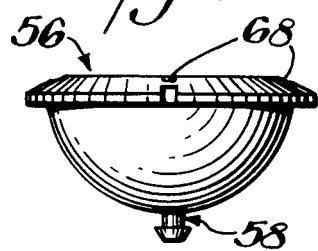
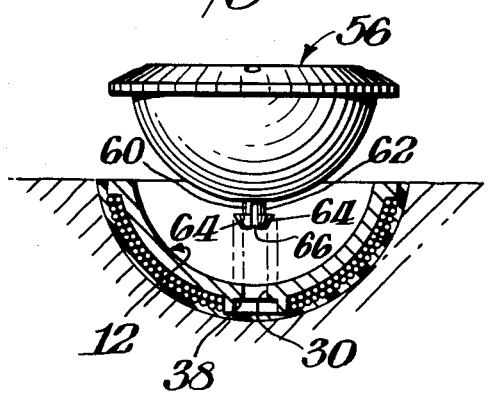
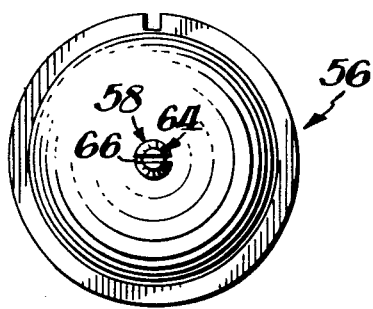
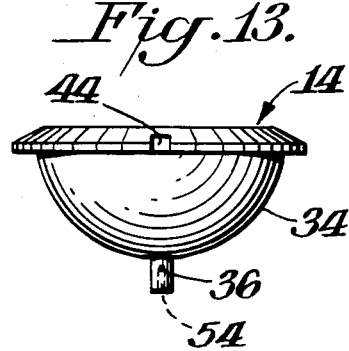

ACETABULAR CUP ASSEMBLY PROSTHESIS

BACKGROUND OF THE INVENTION

The present invention relates to artificial hip joints and more particularly to an acetabular cup assembly having a socket insert that articulates with the rounded head of a femoral prosthesis.

Total hip arthroplasty includes replacement of the diseased acetabulum with an acetabular cup prosthesis, and numerous arrangements have been proposed for this purpose. U.S. Pat. Nos. 4,262,369, 3,874,003, 3,875,593 and 3,818,512 describe various prostheses for the acetabulum, the latter two patents illustrating a plurality of blades mounted in tiers for interaction with the body tissue of the pelvis and a threaded nut for maintaining a hinged connection between the prosthesis for the acetabulum and that for the femur. Also, U.S. Pat. No. 3,685,058 discloses an artificial socket with a nail on the outside thereof for anchoring the socket to the pelvis. Other types of prosthesis for the acetabulum are shown in French Pat. No. 2 377 798 (Application Ser. No. 77 01530) and German Offenlegungsschrift No. 23 49 357. U.S. Pat. No. 230,429 illustrates an acetabular cup with a plurality of knobs on the exterior surface. For the most part, these arrangements appear difficult to use and unduly complicated in design and function.

SUMMARY OF THE INVENTION

Accordingly, an object of the present invention is to provide an acetabular cup assembly prosthesis comprising a support shell and socket insert that articulates with the rounded head of a femoral prosthesis in a highly reliable manner, the assembly being free of complexity and easy to position in the acetabulum.

Another object of the present invention is an acetabular cup assembly prosthesis wherein the socket insert may be replaced by a relatively simple procedure without removal of the support shell from the acetabulum.

In accordance with the present invention, an acetabular cup assembly prosthesis comprises the combination of a support shell for introduction into an acetabulum and a socket insert in nesting engagement within the shell. The shell has a generally hemispherical outer surface and a downwardly extending concavity surrounded by a peripheral rim. At least one anchoring post on the outside of the shell extends downward from the peripheral rim for securing the shell to an acetabulum. A central opening in the bottom of the concavity serves as a connection location for the socket insert. The insert has a hemispherical concavity that articulates with the rounded head of a femoral prosthesis and an outer surface that nests within the concavity of the support shell. A central fastening tab extends downward from the outer surface of the insert into locking engagement with the central opening in the support shell. Structure is provided on the shell and insert for preventing relative rotation about an axis that passes through the geometric center of the hemispherical concavity of the insert and the central opening in the shell.

Preferably, the concavity in the support shell is generally hemispherical and the peripheral rim portion thereof is annular. Also, the socket insert has an outwardly extending brim engaging the peripheral rim of the support shell.

The structure on the support shell and socket insert that prevents relative rotation may include a slot in the brim of the insert and a raised lug on the peripheral rim of the shell positioned within the slot. Preferably, a pair of spaced apart anchoring posts are provided on the outside of the support shell, the posts being spaced either 90° or 45° apart. In some cases a single post is satisfactory, while in other cases two or three posts may be required.

The central opening in the support shell includes an undercut and the fastening tab on the outside of the socket insert has an outwardly extending portion in engagement with the undercut to thereby lock the insert to the shell. In the replacement form of insert, the central fastening tab is bifurcated into two flexible branch portions, each having an outwardly extending locking lip in engagement with the undercut of the support shell. This form of fastening tab is particularly useful with a replacement insert, since use thereof does not require removal of the support shell from the acetabulum. Instead, the original socket insert is removed and the replacement conveniently substituted therefor.

The exterior surface of the support shell may have a porous coating thereon to aid in anchoring the shell to the acetabulum. Moreover, the support shell is preferably fabricated from metal while the socket insert is made of high density polyethylene.

BRIEF DESCRIPTION OF THE DRAWING

Novel features and advantages of the present invention in addition to those mentioned above will become apparent to those skilled in the art from a reading of the following detailed description in conjunction with the accompanying drawing wherein:

FIG. 1 is a front elevational view of an acetabular cup assembly prosthesis, according to the present invention;

FIG. 2 is a top plan view of the prosthesis;

FIG. 3 is a bottom plan view of the prosthesis;

FIG. 4 is a right side elevational view of the prosthesis;

FIG. 5 is a left side elevational view of the prosthesis;

FIG. 6 is a right side elevational view of the prosthesis rotated 45° in a counterclockwise direction;

FIG. 7 is a sectional view taken along line 7—7 of FIG. 2;

FIG. 8 is a front elevational view of a replacement insert for the original insert of the acetabular cup assembly prosthesis shown in FIGS. 1-7;

FIG. 9 is a top plan view of the replacement insert;

FIG. 10 is a bottom plan view of the replacement insert;

FIG. 11 is an exploded elevational view of the replacement insert with the support shell of the original assembly shown in section within an acetabulum;

FIG. 12 is an elevational view of the replacement insert fastened to the support shell of the original assembly with the shell shown in section within an acetabulum;

FIG. 13 is a front elevational view of the insert of the original assembly illustrating the fastening tab prior to deformation;

DETAILED DESCRIPTION OF THE INVENTION

Figure 15:
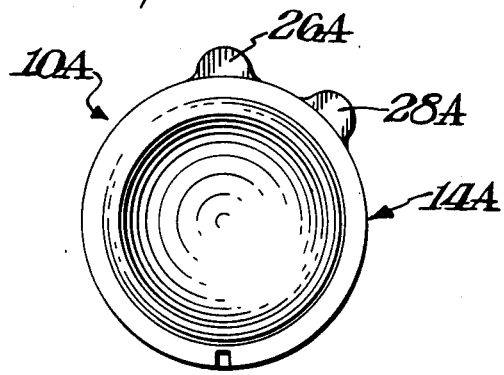
FIG. 15 is a top plan view of the prosthesis shown in FIG. 14.
Figure 14:
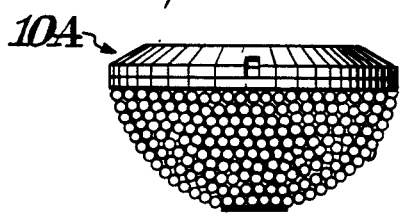
FIG. 14 is a front elevational view of an alternative form of the prosthesis showing a pair of anchoring posts spaced 45° apart.
Figure 17:
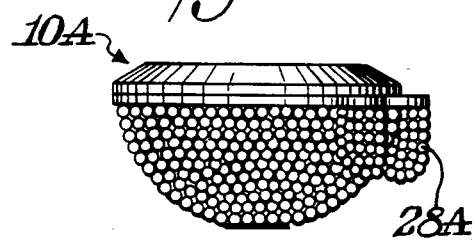
FIG. 17 is a right side elevational view of the prosthesis shown in FIG. 14.
Figure 16:
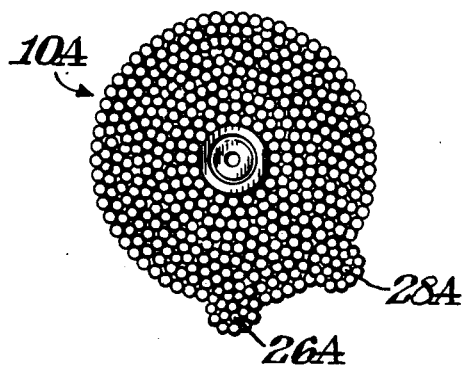
FIG. 16 is a bottom plan view of the prosthesis shown in FIG. 14.
Figure 18:
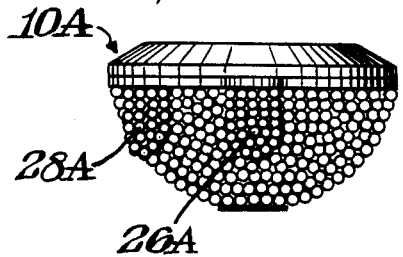
FIG. 18 is a rear elevational view of the prosthesis shown in FIG. 14.

Referring in more particularity to the drawing, FIGS. 1-7 illustrate an acetabular cup assembly prosthesis 10 comprising a support shell 12 and a socket insert 14 arranged for nesting engagement within the support shell 12. The prosthesis 10 serves as a replacement for the natural acetabular cup and is constructed for introduction into an acetabulum 16 in the pelvis 18. The prosthesis 10 may be used on either the right or left side of the pelvis 18, being introduced into the acetabulum 16 after appropriate preparation thereof. Such preparation normally includes reaming of the acetabulum 16, and, in the case of the present invention, drilling of appropriate anchoring holes, as explained more fully below.

The support shell 12 of the prosthesis 10 has a downwardly extending concavity 20 surrounded by a peripheral rim portion 22. Preferably, the concavity 20 is generally hemispherical in shape and the peripheral rim portion 22 is annular. The support shell 12 has a generally hemispherical outside surface 24 that complements the acetabulum 16. A pair of spaced apart anchoring posts 26,28 on the outside of the support shell 12 are positioned adjacent the peripheral rim portion 22 and extend downward therefrom for securing the support shell 12 within the acetabulum 16, as explained below. The posts 26,28 are positioned 90° apart. A central opening 30 in the bottom of the concavity 20 serves to connect the socket insert 14 to the support shell 12.

The socket insert 14 has a hemispherical concavity 32 that articulates with the rounded head of a femoral prosthesis and an outer surface 34 that nests within the concavity 20 of the support shell 12. A central fastening tab 36 extends downwardly from the outer surface 34 of socket insert 14 into opening 30 in locking engagement with support shell 12. As explained more fully below, support shell 12 includes an undercut 38 adjacent opening 30, and an outwardly extending portion 40 on fastening tab 36 is in engagement with the undercut 38.

As shown best in FIG. 7, an outwardly extending brim portion 42 on socket inset 14 engages the peripheral rim portion 22 of support shell 12 to assist fastening tab 36 in preventing rocking movement of socket insert 14 relative to support shell 12.

Relative rotation of socket insert 14 and support shell 12 about an axis that passes through the geometric center of the hemispherical concavity 32 and the opening 30 is prevented by interlocking structure on the socket insert 14 and support shell 12. Specifically, the socket insert 14 includes a slot 44 in the brim portion 42, and a raised lug 46 on the peripheral rim portion 22 of the support shell 12 fits within the slot 44.

The outside surface 24 of support shell 12 has a porous coating 48 for bone ingrowth or for interlocking with bone cement 50 after prosthesis 10 is introduced into the acetabulum 16. Preferably, the support shell 12 is fabricated from metal, such as cobalt/chromium/molybdenum or titanium, and the socket insert 14 is made of high density polyethylene, for example, by molding and/or forming techniques known in the art.

The acetabulum 16 is prepared to receive prosthesis 10 by initially reaming the acetabulum 16 until it dimensionally complements the prosthesis 10. The next step involves drilling or otherwise forming two holes 52 in the pelvis 18 sized and oriented to receive the anchoring posts 26,28 of the support shell 12. Preferably, each hole 52 is sized to provide a tight fit with the anchoring past 26,28 and the depth is such that when the anchoring posts 26,28 bottom out in the holes 52, the support shell 12 is generally flush with the pelvis 18. The overall interrelationship between the holes 52 and the anchoring posts 26,28 provides a uniform spacing between the reamed acetabulum 16 and the outside surface 24 of the support shell 12. Hence, when bone cement 50, such as methyl methacrylate, is used to assist in anchoring the prosthesis 10 within the acetabulum 16, a uniform distribution of the cement 50 results.

As explained above, the fastening tab 36 positively secures the socket insert 14 to the support shell 12 and prevents rocking of the socket insert 14 relative to the support shell 12. Additionally, interaction between the brim portion 42 of the socket insert 14 and the peripheral rim portion 22 of the support shell 12 also prevents the socket insert 14 from rocking with the support shell 12. The brim portion 42 resting upon the peripheral rim portion 22 prevents rocking movement of socket insert 14 relative to support shell 12 in all directions. Moreover, engagement between brim portion 42 and peripheral rim portion 22 eliminates any lateral shear force that might otherwise be placed on the fastening tab 36 by support shell 12.

Prior to positioning the prosthesis 10 within the prepared acetabulum 16, the polyethylene socket insert 14 is secured to the metal support shell 12. This is accomplished by initially joining the two elements with the slot 44 in the brim portion 42 located directly over the raised lug 46 in the peripheral rim portion 22. The fastening tab 36 is then urged into and through opening 30 in support shell 12. Ultrasonic welding or other means is utilized to deform the fastening tab 36 and urge the portion 40 thereof into engagement with the undercut 38 at the opening 30. The fastening tab 36 may have a small central void 54 therein to facilitate deformation at the time of assembly, as shown best in FIG. 13 wherein socket insert 14 is shown prior to assembly.

At some time after prosthesis 10 is secured within the acetabulum 16, it may become necessary to replace the socket insert 14. In accordance with the present invention, such replacement is accomplished with a slightly modified insert and without removing the support shell 12 from its anchored position within the acetabulum 16.

FIGS. 8-12 illustrate a replacement socket insert 56 for performing this procedure, and since the replacement socket insert 56 is quite similar to the original socket insert 14, similar parts are identified with similar reference numerals. The replacement socket insert 56 differs from the original socket insert 14 in that it has a modified fastening tab 58 comprising two flexible branch portions 60,62 separated by a slot 64. Each branch portion 60,62 has an outwardly extending locking lip 66 at its free end that cooperates with the undercut 38 in the support shell 12, as explained more fully below. Moreover, the ends of branch portions 60,62 are inclined in such a manner that the branch portions 60,62 move toward one another as modified fastening tab 58 is forced through opening 30 in support shell 12. The replacement socket insert 56 includes a series of holes 68 in the top surface thereof arranged to receive a handling tool (not shown) to facilitate assembly of the replacement socket insert 56 and the support shell 12.

The original socket insert 14 is removed from the support shell 12 by drilling or otherwise removing material from the bottom of the socket insert 14 to thereby unlock the fastening tab 36 from the undercut 38 in the support shell 12. After the original socket insert 14 is removed from the support shell 12, including the portions 40 of the fastening tab 36 which are often separated by the drilling procedure, the replacement socket insert 56 is urged into the concavity 20 until the modified fastening tab 58 enters opening 30 in support shell 12. The replacement socket insert 56 may then be rotated relative to the support shell 12 to align the slot 44 in the brim portion 42 and the raised lug 46 in the peripheral rim portion 22, assuming this has not already been accomplished. Urging the replacement socket insert 56 further into the support shell 12 causes the inclined ends of the branch portions 60,62 to engage the periphery of the opening 30; continued movement causes the branch portions 60,62 to move toward one another, which allows the locking lips 66 to pass through the opening 30. Once the locking lips 66 clear the opening 30, the branch portions 60,62 spring back to their normal positions and the locking lips 66 are locked in the undercut 38 of support shell 12. As can readily be understood, the replacement socket insert 56 then functions in the same manner as the original socket insert 14. This procedure eliminates the need for further reaming and enlargement of the acetabulum 16 which might otherwise be required if the entire prosthesis 10 were replaced.

FIGS. 14-18 illustrate an acetabular cup assembly prosthesis 10A similar in all respects to prosthesis 10 except for the spacing between the anchoring posts. Specifically, prosthesis 10A has a pair of anchoring posts 26A,28A spaced 45° apart. Similar parts are identified by similar reference numerals, it being understood that the interaction between the support shell 12 and socket insert 14 of prosthesis 10A is the same as with prosthesis 10. Also, socket insert 14 of prosthesis 10A may be removed and replaced with insert 56 in the same manner as described above. Obviously, when the acetabulum 16 is prepared to receive prosthesis 10A the holes 52 in the pelvis 18 are spaced 45° apart rather than 90°. Otherwise, the procedure is the same.

Figure 19:
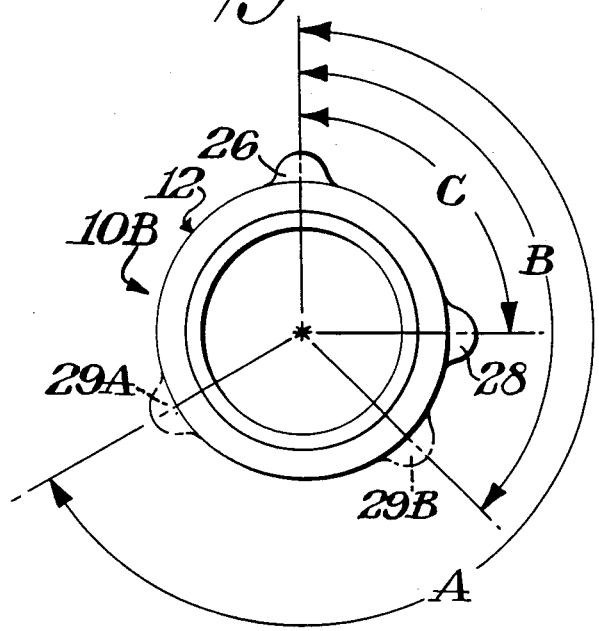
FIG. 19 is a diagrammatic top plan view illustrating a prosthesis with three anchoring posts.

FIG. 19 diagrammatically illustrates a prosthesis 10B similar in all respects to prosthesis 10 except for the provision of a third anchoring post 29. Post 29 may be spaced from post 26 by angle A or by angle B or by some angular amount therebetween while posts 26 and 28 are spaced from each other by angle C. Specifically, angle A may be 240° with angles B and C 135° and 90°, respectively. When the third post 29 is 29A, the three posts extend over 240° (angle A) of the peripheral boundary of shell 12, while with post 29B the posts are more closely spaced, extending over 135° (angle B) of the shell boundary. Alternatively, the third post 29 may be located between 29A and 29B. With this arrangement, the uninterrupted peripheral boundary of the shell 12 is at least 120° and may be as much as 225°. Depending upon the condition of the pelvis surrounding the natural acetabulum 16, one, two or three anchoring posts may be used to secure the prosthesis in place.

Figure 20:
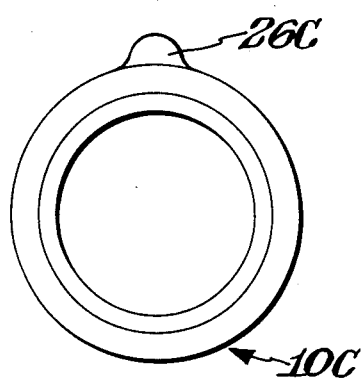
FIG. 20 is a top plan view of an alternative form of the prosthesis showing a single anchoring post, according to the present invention.

FIG. 20, for example, shows prosthesis 10C having a single post 26C.

I claim:

1. An acetabular cup assembly prosthesis, which comprises a combination of a hollow hemispherical support shell surrounded by a peripheral rim for attachment into a prepared acetabulum and a complementary shaped socket insert for cooperative engagement within the support shell;

the support shell having at least one anchoring post formed on an outer shell surface adjacent the peripheral rim and extending outwardly from the outer shell surface for securing the support shell within the prepared acetabulum, and the support shell further including a central opening formed in an apex region thereof wherein a portion of the support shell directly adjacent to the central opening is formed with an undercut flange for connecting the socket insert to the support shell;

the socket insert having an inner hemispherical cavity and an outer surface adapted to fit within the support shell wherein the socket insert includes a central fastening tab extending outwardly from the outer insert surface and dimensioned so as to be inserted into engagement with the central opening, the central fastening tab having transverse outwardly extending portions that lockingly engage with the undercut flange thereby providing the sole means of attaching the socket insert to the support shell;

means formed on the support shell and socket insert preventing relative rotation of the socket insert and support shell about an axis that passes through the geometric center of the hemispherical cavity of the socket insert and the central opening in the support shell.

2. An acetabular cup assembly prosthesis as in claim 1 wherein the concavity in the support shell is generally hemispherical and the peripheral rim portion is annular.

3. An acetabular cup assembly prosthesis as in claim 1 wherein the socket insert includes an outwardly extending brim engaging the peripheral rim of the support shell.

4. An acetabular cup assembly prosthesis as in claim 3 wherein the means formed on the support shell and socket insert preventing relative rotation includes a slot in the brim of the socket insert and a raised lug on the peripheral rim of the support shell positioned within the slot.

5. An acetabular cup assembly prosthesis as in claim 1 including a pair of spaced apart anchoring posts formed on the outer surface of the support shell.

6. An acetabular cup assembly prosthesis as in claim 5 wherein the anchoring posts are spaced 90° apart.

7. An acetabular cup assembly prosthesis as in claim 5 wherein the anchoring posts are spaced 45° apart.

8. An acetabular cup assembly prosthesis as in claim 1 including three spaced apart anchoring posts formed on the outer surface of the support shell.

9. An acetabular cup assembly prosthesis as in claim 8 wherein the three anchoring posts collectively are spaced from 135° to 240° apart.

10. An acetabular cup assembly prosthesis as in claim 1 including a single anchoring post formed on the outer surface of the support shell.

11. An acetabular cup assembly prosthesis as in claim 1 wherein the central fastening tab is bifurcated into two flexible branch portions, each having an outwardly extending locking lip in engagement with the undercut flange.

12. An acetabular cup assembly prosthesis as in claim 1 wherein the outer surface of the support shell has a porous coating thereon.

13. An acetabular cup assembly prosthesis as in claim 1 wherein the support shell is metal and the socket insert is high density polyethylene.

* * * * *